(12) United States Patent
Whatcott et al.

(10) Patent No.: US 7,374,569 B2
(45) Date of Patent: May 20, 2008

(54) DYNAMICALLY DISTRIBUTING POWER OF A LIGHT BEAM FOR USE IN LIGHT THERAPY

(75) Inventors: Gary L. Whatcott, Holladay, UT (US); Forrest L. Williams, Sandy, UT (US)

(73) Assignee: DYNATRONICS, Corporation, Salt Lake City, UT (US)

( * ) Notice: Subject to any disclaimer, the term of this patent is extended or adjusted under 35 U.S.C. 154(b) by 335 days.

(21) Appl. No.: 10/933,032

(22) Filed: Sep. 2, 2004

(65) Prior Publication Data

US 2006/0047330 A1 Mar. 2, 2006

(51) Int. Cl.
*A61N 5/067* (2006.01)
(52) U.S. Cl. ............... 607/89; 128/898; 607/88
(58) Field of Classification Search ............. 128/898; 607/88–94
See application file for complete search history.

(56) References Cited

U.S. PATENT DOCUMENTS

| | | | |
|---|---|---|---|
| 3,096,768 A | 7/1963 | Griffith, Jr. | |
| 3,774,620 A | 11/1973 | Hansjurgens | |
| 3,895,639 A | 7/1975 | Rodler | |
| 3,958,577 A | 5/1976 | Rodler | |
| 4,023,574 A | 5/1977 | Nemec | |
| 4,071,033 A | 1/1978 | Nawracaj et al. | |
| 4,153,061 A | 5/1979 | Nemec | |
| 4,280,504 A | 7/1981 | Rodler | |
| 4,368,410 A | 1/1983 | Hance et al. | |
| 4,535,777 A | 8/1985 | Castel | |
| 4,538,598 A | 9/1985 | Gill et al. | |
| 4,564,019 A | 1/1986 | Miwa | |
| 4,747,820 A | 5/1988 | Hornlein et al. | |
| 4,768,496 A | 9/1988 | Kreizman et al. | |
| 4,848,347 A | 7/1989 | Hall | |
| 4,930,504 A | 6/1990 | Diamantopoulos et al. | 128/395 |
| 4,966,131 A | 10/1990 | Houghton et al. | |
| RE33,672 E | 8/1991 | Miwa | |
| 5,151,085 A | 9/1992 | Sakurai et al. | |
| 5,184,605 A | 2/1993 | Grzeszykowski | |
| 5,269,304 A | 12/1993 | Matthews | |
| 5,460,595 A | 10/1995 | Hall et al. | |
| 5,512,057 A | 4/1996 | Reiss et al. | |
| 5,620,481 A | 4/1997 | Desai et al. | |
| 5,776,173 A | 7/1998 | Madsen, Jr. et al. | |
| 5,995,873 A | 11/1999 | Rhodes | |
| 6,197,020 B1* | 3/2001 | O'Donnell, Jr. | 606/9 |
| 6,252,714 B1* | 6/2001 | Guenther et al. | 359/559 |
| 6,393,328 B1 | 5/2002 | McGraw et al. | |
| 6,560,487 B1 | 5/2003 | McGraw et al. | |
| 6,728,036 B2* | 4/2004 | Kleemann et al. | 359/575 |
| 6,826,429 B2 | 11/2004 | Johnson et al. | |

(Continued)

*Primary Examiner*—Henry M Johnson, III
(74) *Attorney, Agent, or Firm*—Kirton & McConkie; David B. Tingey

(57) ABSTRACT

Systems and methods for dynamically distributing power of a light beam for use in administering light therapy. A laser light beam having a maximum peak power is selectively diffused to distribute the maximum peak power. In at least some implementations, the diffused laser light beam is attenuated across the diffused beam. Having undergone processes of diffusion and attenuation, the laser light beam is then safely used to administer light therapy on a patient. In further implementations, the diffusion includes a defocused diffusion and/or includes a distribution of power rather than an attenuation of power.

26 Claims, 8 Drawing Sheets
(2 of 8 Drawing Sheet(s) Filed in Color)

U.S. PATENT DOCUMENTS

| | | | |
|---|---|---|---|
| 6,909,546 B2 * | 6/2005 | Hirai | 359/566 |
| 6,942,658 B1 * | 9/2005 | Rizoiu et al. | 606/16 |
| 7,077,544 B2 * | 7/2006 | Parker | 362/252 |
| 7,118,563 B2 * | 10/2006 | Weckwerth et al. | 606/9 |
| 2004/0136665 A1 * | 7/2004 | Furman et al. | 385/115 |
| 2004/0184287 A1 * | 9/2004 | Smith et al. | 362/560 |
| 2004/0260367 A1 * | 12/2004 | De Taboada et al. | 607/88 |
| 2005/0234527 A1 * | 10/2005 | Slatkine | 607/89 |
| 2006/0100676 A1 * | 5/2006 | Walmsley | 607/89 |

* cited by examiner

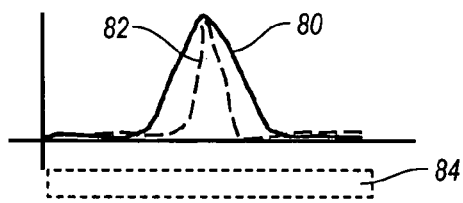
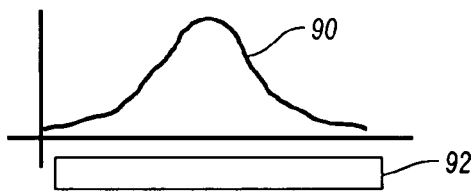
Fig. 11          Fig. 12
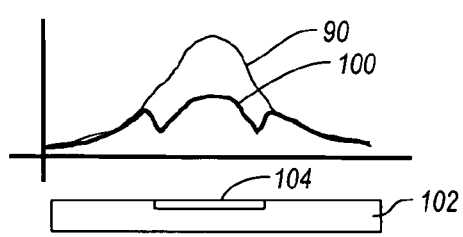
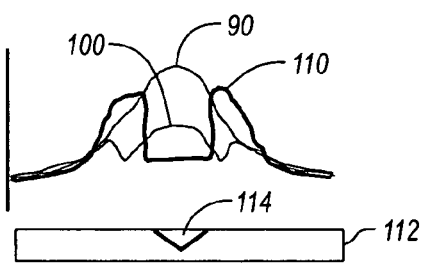
Fig. 13          Fig. 14
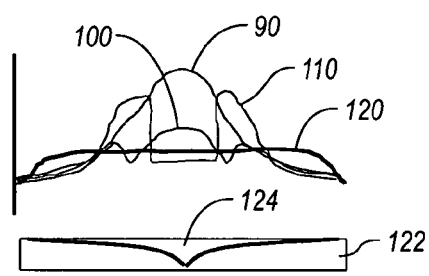
Fig. 15

DYNAMICALLY DISTRIBUTING POWER OF A LIGHT BEAM FOR USE IN LIGHT THERAPY

BACKGROUND OF THE INVENTION

1. Field of the Invention

The present invention relates to light therapy. In particular, the present invention relates to systems and methods for dynamically distributing power of a light beam for use in administering light therapy.

2. Background and Related Art

High-powered lasers generally emit collimated, coherent light that has been used to cut and/or burn away tissue, such as in surgical techniques. More recently, low-powered light sources that do not sever or destroy tissue have been used with the intention to provide an effect on a variety of metabolic processes. For example, the low-powered light sources are used in pain and chronic pain management, sports medicine, dermatology, rheumatology and dentistry.

While low powered light sources emit photons that may be used to interact with biological molecules to provide photochemical reactions and/or biologic effects, only the photons that are actually absorbed provide photochemical reactions. X-rays, gamma rays and other absorbed high-energy photons affect human tissues by relatively indiscriminate ionization of molecules.

With the use of current low powered light source techniques, it is difficult to expose more than the first few layers of human skin or tissue to visible and ultraviolet radiation since pigments and other molecules located in the surface layers of the skin absorb the majority of visible and ultraviolet radiation. Accordingly, applying visible and ultraviolet radiation to the skin may have little or no effect on target molecules in lower layers that could become stimulated if exposed to those wavelengths of radiation. And, while higher powered radiation sources can deliver greater energy to deeper layers, it is undesirable to expose tissue to such large amounts of ultraviolet radiation due to the adverse effects of such concentrated radiation.

Thus, while techniques currently exist that are used to provide light therapy, challenges still exist. Accordingly, it would be an improvement in the art to augment or even replace current techniques with other techniques.

SUMMARY OF THE INVENTION

The present invention relates to light therapy. In particular, the present invention relates to systems and methods for dynamically distributing power of a light beam for use in administering light therapy.

In at least some implementations of the present invention, light therapy is made available or otherwise provided by the use of one or more light sources. In at least some implementations one or more of the light sources are laser light sources, such as laser diodes. The light beam power of the laser light source is dynamically distributed to provide an influence on metabolism-related processes without the destruction of tissue.

In at least some implementations of the present invention, a laser light beam having a maximum peak power is selectively diffused to distribute the maximum peak power. In at least some implementations, the diffused laser light beam is attenuated across the diffused beam. Having undergone processes of diffusion and attenuation, the laser light beam is then safely used to administer light therapy on a patient. In further implementations, the diffusion includes a defocused diffusion.

Examples of light therapy treatment in accordance with the present invention include use of the systems and/or methods of the present invention for the treatment of an injury, tension headaches, chronic pain, migraine headaches, tension headaches, atypical facial pain, TMJ disorders, occipital neuralgia, neck-shoulder pain, fibromyalgia, medial epicondylitis, lateral epicondylitis, carpal tunnel syndrome, osteoarthritis, rheumatoid arthritis, pain and/or stiffness associated with arthritis, muscle spasm, costochondritis, spondylitis, low back strain, joint pain, sciatica, achilles tendonitis, ankle sprain, plantar fasciitis, shingles, Raynaud's Syndrome, reflex sympathetic dystrophy (also known as chronic regional pain syndrome), postherpetic neuralgia, burns, inflammation, pain, muscle spasm, wound healing, and the like.

While the methods and processes of the present invention have proven to be particularly useful in the areas of pain management and wound healing, those skilled in the art can appreciate that the methods and processes can be used in a variety of different applications and in a variety of different areas of manufacture to enable or otherwise provide light therapy utilizing laser light sources.

These and other features and advantages of the present invention will be set forth or will become more fully apparent in the description that follows and in the appended claims. The features and advantages may be realized and obtained by means of the instruments and combinations particularly pointed out in the appended claims. Furthermore, the features and advantages of the invention may be learned by the practice of the invention or will be obvious from the description, as set forth hereinafter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In order that the manner in which the above recited and other features and advantages of the present invention are obtained, a more particular description of the invention will be rendered by reference to specific embodiments thereof, which are illustrated in the appended drawings. Understanding that the drawings depict only typical embodiments of the present invention and are not, therefore, to be considered as limiting the scope of the invention, the present invention will be described and explained with additional specificity and detail through the use of the accompanying drawings in which:

FIG. 11 illustrates a graphical representation of a raw laser output;

FIG. 12 illustrates a graphical representation of a laser output, wherein the laser is transmitted through a holographic diffuser;

FIG. 13 illustrates a graphical representation of a laser output, wherein the laser is transmitted through a holographic diffuser and disk attenuator;

FIG. 14 illustrates a graphical representation of a laser output, wherein the laser is transmitted through a holographic diffuser and counter sink diffraction component;

FIG. 15 illustrates a graphical representation of a laser output, wherein the laser is transmitted through a holographic diffuser and compound counter sink diffraction component;

DETAILED DESCRIPTION OF THE INVENTION

The present invention relates to light therapy. In particular, the present invention relates to systems and methods for dynamically distributing power of a light beam for use in administering light therapy.

Embodiments of the present invention relate to biostimulation and/or other forms of light therapy being made available or otherwise provided for by the use of one or more laser light sources, such as laser diodes. The light beam power of the laser light source is dynamically distributed to provide an influence on metabolism-related processes without the destruction of tissue.

In the disclosure and in the claims the term "substantially uniform" shall refer to manipulating a laser beam to increase the uniformity of the power distribution across a profile or surface area of the laser beam. Examples of manipulating the laser beam include one or more processes of diffusing the laser beam and/or one or more processes of attenuating the laser beam.

Thus, in at least some embodiments, a laser light beam having a maximum peak power is diffused to distribute the maximum peak power. In further embodiments, the diffused laser light beam is attenuated across the diffused beam. Having undergone one or more processes of distribution, such as through one or more processes of diffusion and/or attenuation, the laser light beam is then safely used to administer light therapy on a patient.

FIGS. 1-5 and the corresponding discussion are intended to provide a general description of a suitable operating environment in which the invention may be implemented. One skilled in the art will appreciate that the invention may be practiced by one or more devices and in a variety of system configurations.

Figure 1:
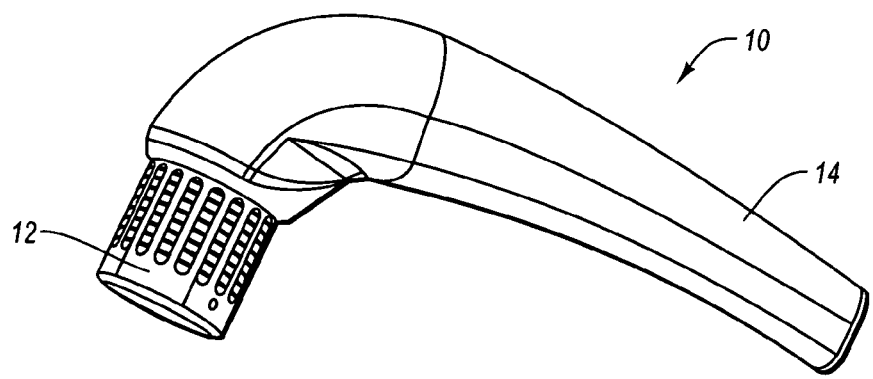
FIG. 1 illustrates a perspective view of a representative system in accordance with an embodiment of the present invention.
Figure 2:
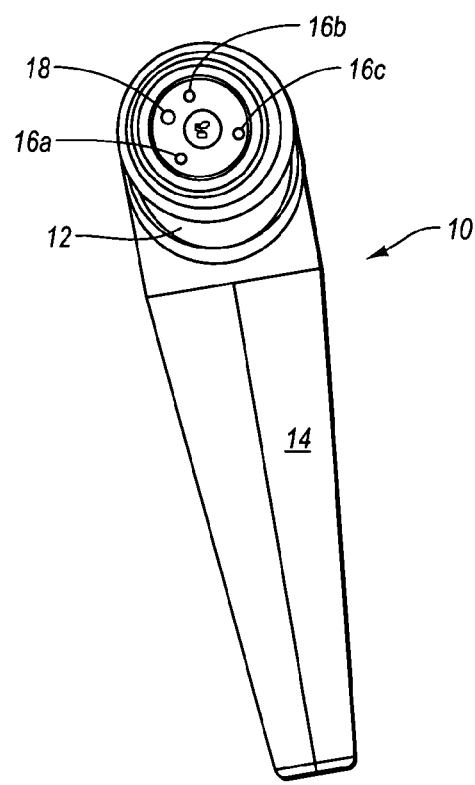
FIG. 2 illustrates a front view of the representative system of FIG. 1.

With reference now to FIG. 1, a perspective view is illustrated of a representative system in accordance with an embodiment of the present invention. In FIG. 1, probe 10 includes head 12 for the administration of laser light and handle 14 to allow a practitioner or other user to control probe 10. As illustrated in FIG. 2, head 12 includes one or more laser light sources, illustrated as laser diodes 16, which provide corresponding laser light beams when actuated. In accordance with embodiments of the present invention, the power of the laser light beams is dynamically distributed to provide one or more substantially uniform beams that are used to influence metabolism-related processes without the destruction of tissue.

In at least some embodiments, probe 10 is coupled to a power source that is used to selectively actuate the laser light sources. In some embodiments, the power source is external to probe 10. In other embodiments, the power source is contained within probe 10.

In the illustrated embodiment, probe 10 also includes a proximity detector to determine the distance between head 12 and the target treatment area of a patient. Light source 18 emits light that is used to measure the distance between head 12 and the target treatment area of a patient. In a further embodiment, light source 18 is further used to provide light therapy.

In at least some embodiments, at least a portion of the light emitted from source 18 is reflected from the surface of the target treatment area and received back by a sensor in head 12. In some embodiments, when the reflected light is received, a notification (e.g., a colored light or other notification) is provided to the user to indicate that head 12 is within treatment range to initiate the light therapy. In further embodiments, the probe is activated when the head is within an established treatment range and/or deactivated when the head is outside the established treatment range.

While the illustrated embodiment of FIG. 2 provides three laser light sources for use in selectively providing light therapy, those skilled in the art will appreciate that embodiments of the present invention embrace systems having more than three laser light sources or systems having less than three laser light sources. Furthermore, embodiments of the present invention embrace the use of multiple light sources to detect the proximity of the head in relation with a target treatment area.

Figure 3:
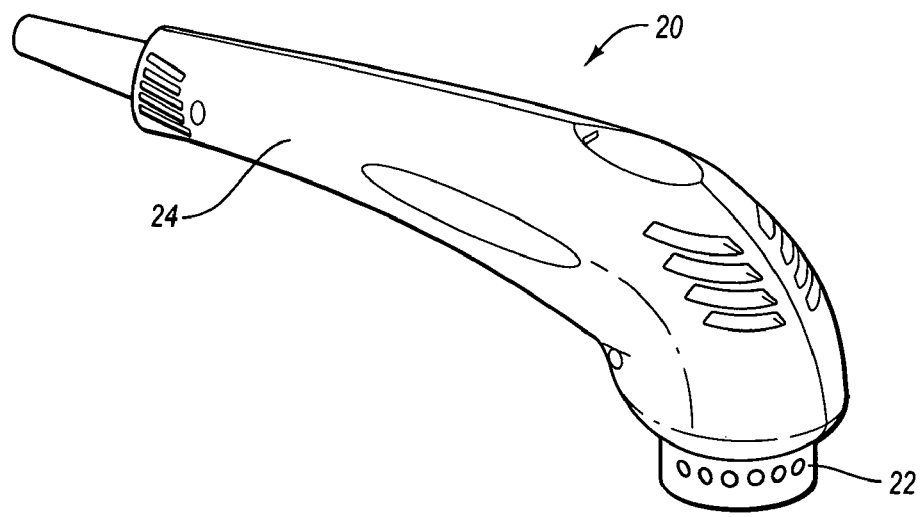
FIG. 3 illustrates a perspective view of another representative system in accordance with an embodiment of the present invention.

With reference now to FIG. 3, a perspective view is illustrated of another representative system in accordance with an embodiment of the present invention. In FIG. 3, probe 20 includes head 22, which comprises one or more laser light sources for use in the administration or light therapy on a target treatment area, and handle 24 to allow the user of probe 20 to selectively direct and control probe 20. As will be further explained below, the dynamic power distribution of the laser light sources spreads out the power across the surface of probe head 22 to provide a substantially uniform power distribution. In the embodiment illustrated in FIG. 3, the surface area of head 22 is approximately 5 cm².

However, those skilled in the art will appreciate that embodiments of the present invention embrace probe heads having smaller or larger surface areas.

Figure 4:
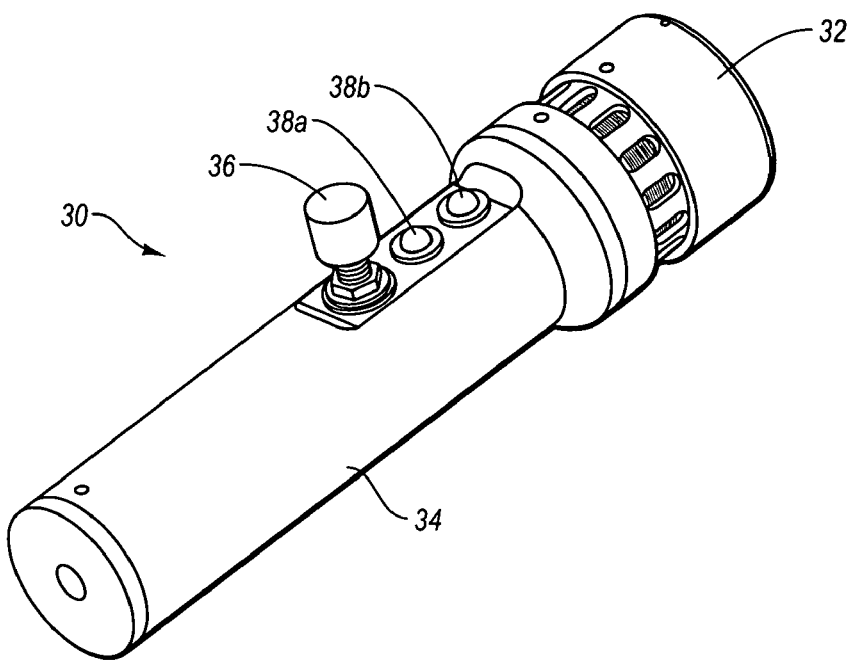
FIG. 4 illustrates a perspective view of another representative system in accordance with an embodiment of the present invention.

With reference now to FIG. 4, another representative system is provided in accordance with an embodiment of the present invention. In FIG. 4, probe 30 includes head 32 for the administration of laser light as light therapy and handle 34 to allow a practitioner or other user to control probe 30. Head 32 includes one or more laser light sources that emit laser light beams when actuated.

Probe 30 includes actuator 36, which selectively turns probe 30 on or off, and indicators 38 to communicate to the user whether or not probe 30 is currently emitting laser light. For example, in one embodiment a green light emitting diode is lit at indicator 38a when probe 30 is actuated and a red light emitting diode is lit at indicator 38b when probe 30 is not actuated. In another embodiment, for example, a green light emitting diode is lit at indicator 38a when probe 30 is determined by a proximity detector to be within treatment range and a red light emitting diode is lit at indicator 38b when probe 30 is not within treatment range.

Figure 5:
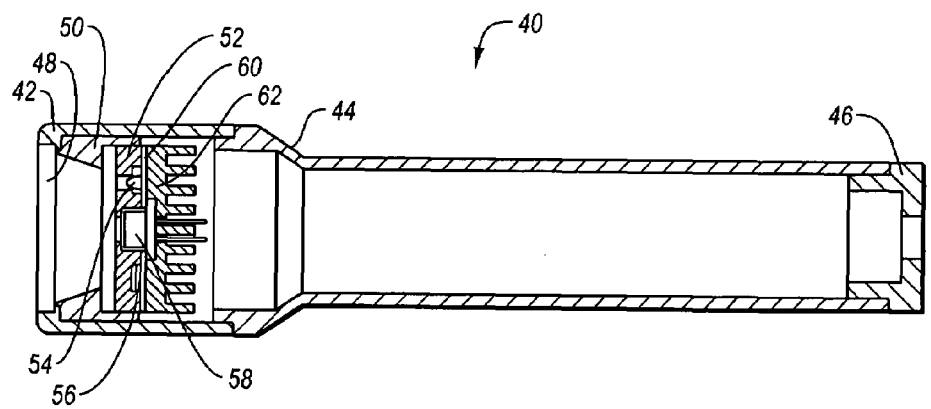
FIG. 5 illustrates a cross-sectional view of another representative system in accordance with an embodiment of the present invention.

With reference now to FIG. 5, a cross-sectional view of an embodiment of the present invention is illustrated. In FIG. 5, a laser light probe 40 is illustrated that may be selectively used to provide light therapy. Probe 40 includes a casing having head portion 42 forming a window, body portion 44 providing a handle and end cap 46. A bezel 48 in head portion 42 is provided to hold a transparent covering or lens (illustrated as lens 49 in FIG. 6). In at least one embodiment, the lens includes a material in the center of the lens to assist in the distribution of power. In a further embodiment, the lens includes a curve to more uniformly distribute power and/or reduce the amount of power attenuated.

Head portion 42 further comprises reflector 50, socket 52, proximity detector light source 54 and corresponding resistor 56, laser light source 58, board 60, and heat sink 62. Probe 40 also includes casing enclosure 42 (e.g., configured to enclose a window, a heat sink, a reflector, and/or similar components), body containing control component(s) 44, end cap means 46 (e.g., configured to close the body and attach a power source), and lens protection element 49 (e.g., configured to cover optical components, a diffusion element, and/or an attenuation element).

Reflector 50 is configured to restrict light to the desired boundary. Socket 52 is a mounting location of PC board 60 that includes such components as proximity detector light source 54, current limiting resistor 56 for light source 54, a photo proximity detector (not shown), and the like.

In the illustrated embodiment, light source 54 is configured to provide treatment power of a differing wavelength. In other embodiments, light source 54 is a laser light source.

Resistor 56 controls or limits current to the proximity detector light source 58. Laser light source 58 is a light treatment source. PC board 60 includes various electrical components or systems, such as proximity detector light source 54, current limiting resistor 56 for light source 54, a photo proximity detector (not show), and the like. Heat sink mounting 62 is for the one or more laser light sources, and provides means to conduct heat from the laser light source(s). Holographic diffuser 59 selectively diffuses light at an incident angle, such as at 30°, 60°, or another angle in all directions. In other embodiments, a holographic diffuser diffuses in different angles that are in perpendicular directions with respect to each other, such as a 95°×25° pattern. In further embodiments, a plurality of diffusers are used in combination, such as a 95°×25° diffusing element in combination with a 30° diffusing element.

Figure 6:
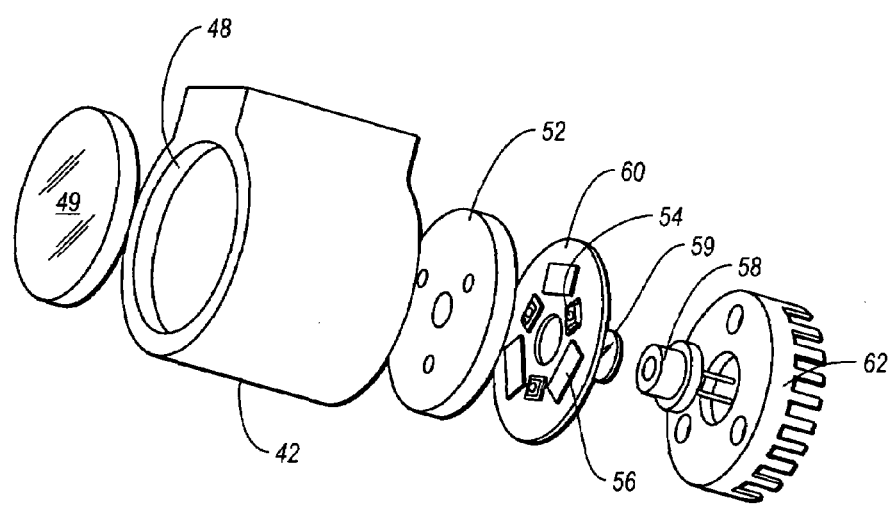
FIG. 6 illustrates an exploded view of various component of the representative system of FIG. 5.

With reference to FIG. 6, an exploded view of various components of the embodiment of FIG. 5 is provided to further illustrate the association of the various components. In FIG. 6, lens 49 is contained by bezel 48 of head portion 42. Heat sink 62 includes an aperture that receives laser diode 58. Disk 59 is a holographic diffuser and attenuator and is configured to couple with laser light source 58 to dynamically distribute the power of the laser light beam generated by laser light source 58. As provided herein, Holographic diffuser 59 selectively diffuses light at an incident angle, such as at 30°, 60°, or another angle in all directions. In other embodiments, a holographic diffuser diffuses in different angles that are in perpendicular directions with respect to each other, such as a 95°×25° pattern. In further embodiments, a plurality of diffusers are used in combination, such as a 95°×25° diffusing element in combination with a 30° diffusing element.

Board 60 is used to provide the circuitry for the proximity detector, such as one or more light sources 54 and one or more resistors 56. Socket 52 corresponds to board 60. As provided above, PC board 60 includes various electrical components or systems, such as proximity detector light source 54, current limiting resistor 56 for light source 54, a photo proximity detector (not show), and the like.

Figure 7:
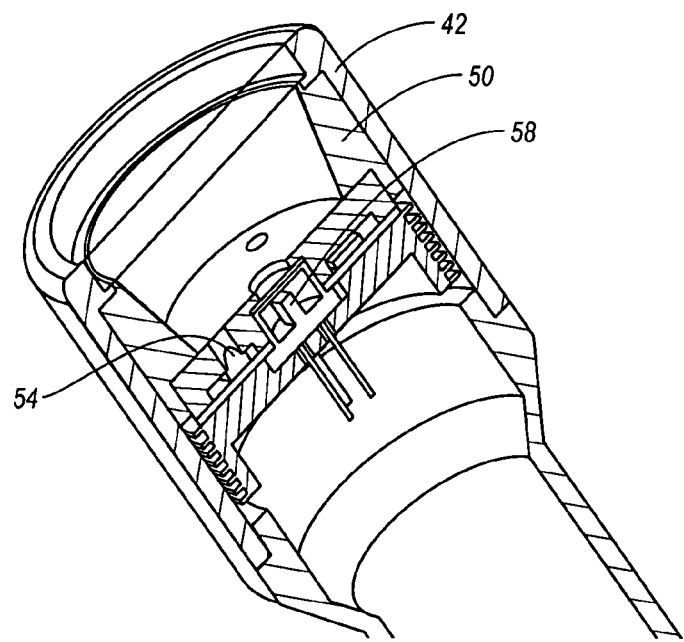
FIG. 7 illustrates a cross-sectional view of a head portion of the representative system of FIG. 5.
Figure 8:
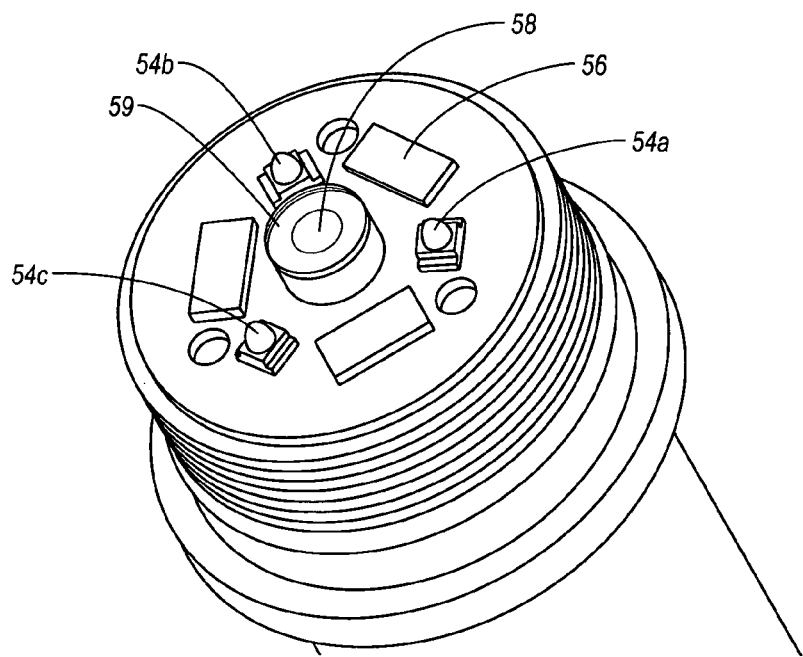
FIG. 8 illustrates various components of the representative system of FIG. 5.

With reference now to FIG. 7, another cross-sectional view of the representative embodiment of FIG. 5 is provided. As illustrated in FIGS. 7-8, head portion 42 (illustrated in FIG. 7) includes a plurality of light sources, including laser light source 58, which is used to provide light therapy, and one or more proximity detector light sources 54, which are used to determine whether the laser light probe head is within range for providing the laser light therapy. In further embodiments the proximity detector light source(s) are further used in providing the laser light therapy.

FIG. 8 further illustrates the association of the holographic diffuser disk 59 with laser light source 58. In one embodiment, light sources 54 are additional light sources for use in administering light therapy. Accordingly, embodiments of the present invention embrace a head that comprises multiple light sources, including laser light sources and/or light emitting diodes. Examples of multiple laser light probe heads will be provided below in connection with FIGS. 9-10. In another embodiment, one or more of light sources 54 are used as part of proximity detector. In yet another embodiment, one or more light sources 54 are used as indicators for the user that the probe is functioning. In further embodiments, a laser light source is used as the light source for the proximity detector.

Figure 9:
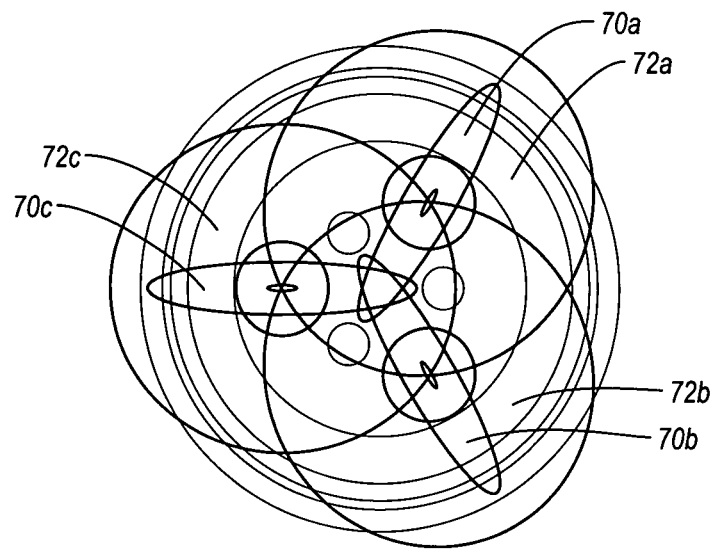
FIG. 9 illustrates a front view of a representative embodiment for dynamically distributing power of a light beam for use in light therapy.
Figure 10:
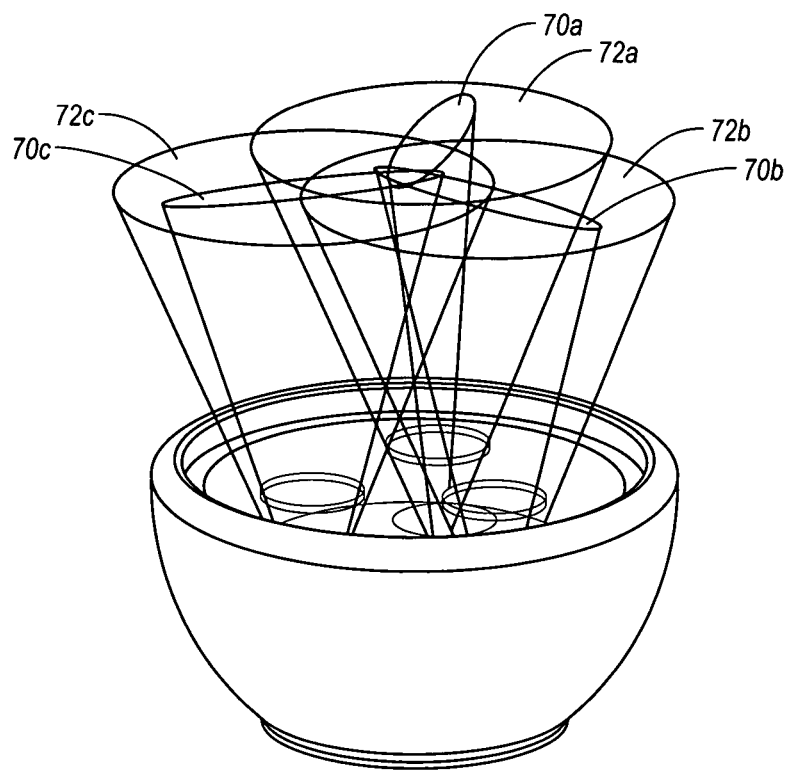
FIG. 10 illustrates a perspective view of a representative embodiment for dynamically distributing power of a light beam for use in light therapy.

As provided herein, embodiments of the present invention relate to systems and methods for dynamically distributing power of a light beam for use in administering light therapy. With reference to FIGS. 9-10, an illustration is provided to detail the dynamic distribution of the laser light beam. As mentioned above, the laser light beam comprises a maximum peak power, which is diffused and/or attenuated to reduce the maximum peak power. The attenuated laser light beams 70 are diffused to distribute power across the attenuated beams 70. In one embodiment, a laser beam is diffused by a holographic diffuser. In another embodiment, a laser beam is diffused by a lens, such as a lens that comprises a diffusing material and/or a curve. In a further embodiment, a laser beam is diffused by both a holographic diffuser and a lens. In yet a further embodiment, the lens provides a defocusing diffusion.

Having undergone one or more processes of distribution, such as through diffusion and/or attenuation, the distributed laser light beams 72 are then available for safe and effective use for administering light therapy on a patient. In particular, distributed laser light beams 72 increase safe and effective use for administering light therapy, and provide a higher output power over traditional methods.

With reference now to FIGS. 11-15, graphical representations of laser outputs are provided to illustrate the dynamic distribution in accordance with the present invention. FIG. 11 illustrates a graphical representation of a raw laser output, which is not associated with any diffuser. In FIG. 11, curve 80 illustrates the perpendicular axis and curve 82 illustrates the parallel axis of a typical raw laser output divergence. The lack of a diffuser 84 indicates that it is a raw laser output.

With reference now to FIG. 12, curve 90 illustrates a graphical representation of a laser output, wherein the laser is transmitted through a holographic diffuser 92.

In FIG. 13, curve 100 illustrates a graphical representation of a laser output, wherein the laser is transmitted through a holographic diffuser 102 and disk attenuator 104. For illustration purposes, FIG. 13 compares curve 100 with curve 90 of FIG. 12.

In FIG. 14, curve 110 illustrates a graphical representation of a laser output, wherein the laser is transmitted through a holographic diffuser 112 and a counter sink diffraction component 114. For illustration purposes, FIG. 14 compares curve 110 with curves 100 of FIG. 13 and 90 of FIG. 12.

With reference now to FIG. 15, curve 120 illustrates a graphical representation of a laser output, wherein the laser is transmitted through a holographic diffuser (not shown) and compound counter sink diffraction component lens having components 122 and 124. For illustration purposes, FIG. 15 compares curve 120 with curves 110 of FIG. 14, 100 of FIG. 13 and 90 of FIG. 12. As provided herein, at least some embodiments embrace distributing a light source, such as a laser light source, in a manner that includes a lens having a curve to distribute power rather than attenuating the power.

Figure 16:
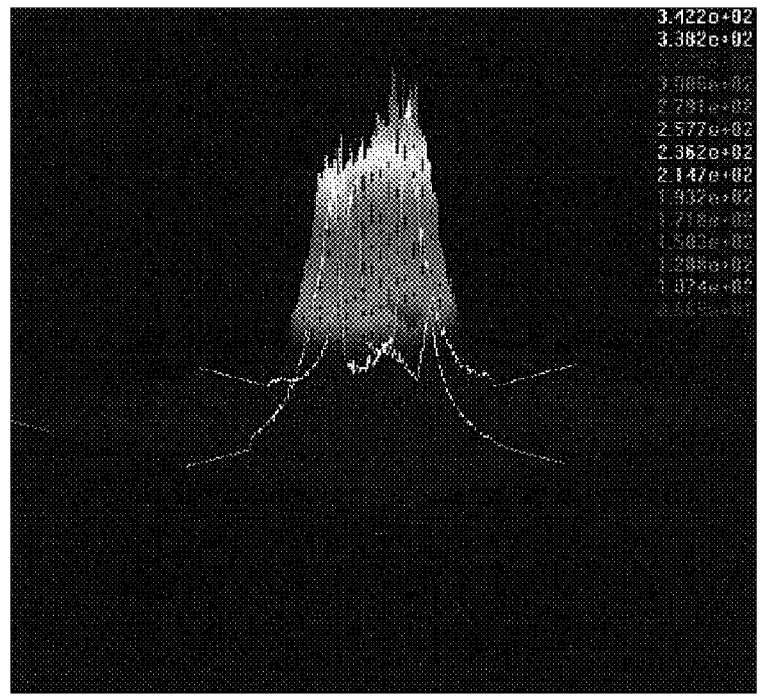
FIG. 16 illustrates a three-dimensional graphical representation of a laser output after the corresponding laser beam has been diffused by a holographic diffuser.
Figure 17:
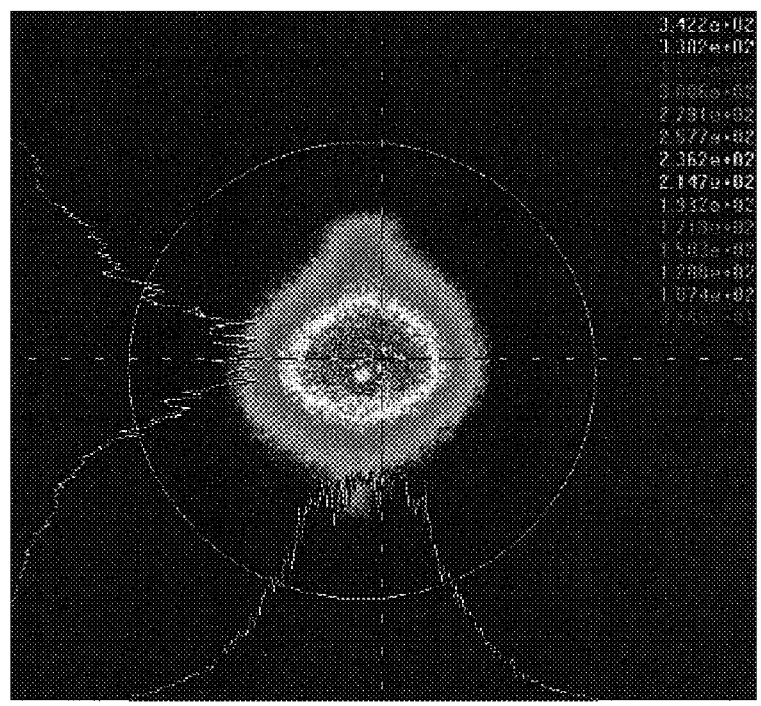
FIG. 17 illustrates a graphical representation of a laser output and corresponding power distribution after the laser beam has been diffused by a holographic diffuser.
Figure 18:
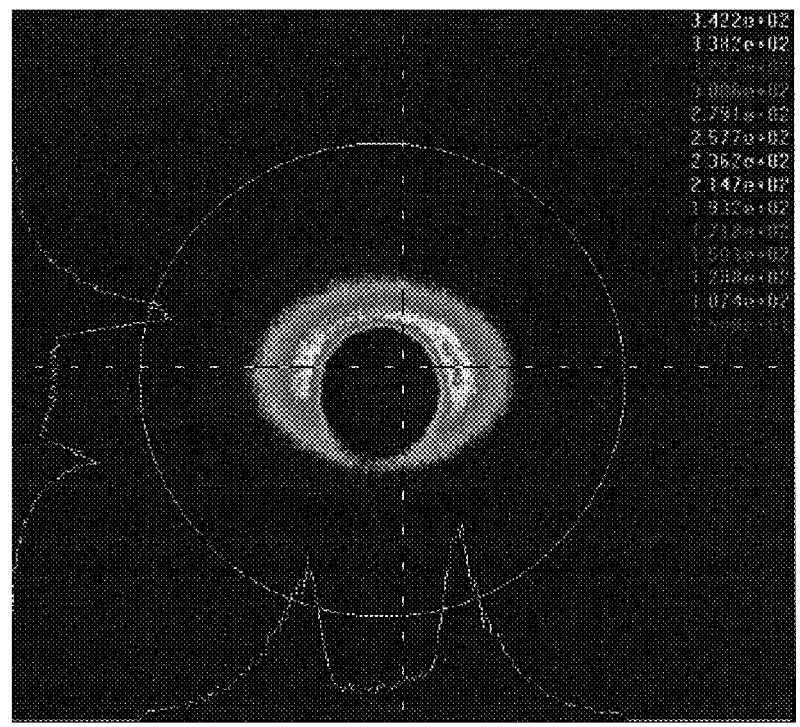
FIG. 18 illustrates a graphical representation of a laser output and corresponding power distribution, wherein the laser is transmitted through a holographic diffuser and counter sink diffraction.

With reference now to FIGS. 16-18, additional graphical representations are provided. In particular, FIG. 16 illustrates a three-dimensional graphical representation of a raw laser output and corresponding peak power. FIG. 17 illustrates a graphical representation of a raw laser output and corresponding power distribution using a 95°×25° holographic diffuser. FIG. 18 illustrates a graphical representation of a laser output and corresponding power distribution, wherein the laser has been transmitted through a 60° holographic diffuser and counter sink diffraction in accordance with an embodiment of the present invention.

Figure 19:
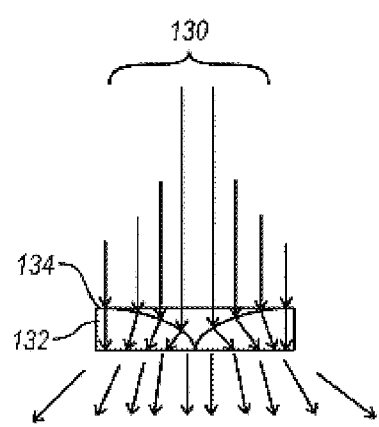
FIG. 19 illustrates a representative optical lens diffusion pattern.

With reference now to FIG. 19, a representative optical lens diffusion pattern is illustrated. In FIG. 19, beam 130 is diffused by optical lens 132, which comprises a curve 134 to distribute power. The length of the ray lines of beam 130 indicates intensity. Thus, longer lines indicate higher intensity.

Figure 20:
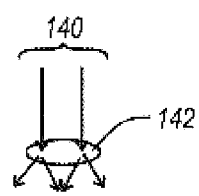
FIG. 20 illustrates a representative holographic diffusion pattern.

With reference now to FIG. 20, a representative holographic diffusion pattern is illustrated. In FIG. 20, beam 140 is diffused by holographic diffuser 142.

Figure 21:
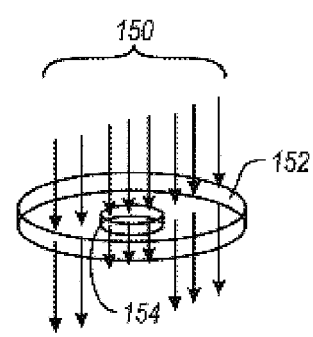
FIG. 21 illustrates a representative attenuation pattern.

With reference now to FIG. 21, a representative attenuation pattern is illustrated. In FIG. 21, beam 150 is attenuated the combination of holographic diffuser 152 and disk attenuator 154. The length of the ray lines of beam 150 indicates intensity. Thus, longer lines indicate higher intensity.

While attenuator 154 is a disk in FIG. 21, those skilled in the art will appreciate that embodiments of the present invention embrace other types of attenuators to attenuate a beam, including other types of configurations, such as a tapered attenuator, etc.

Thus, as discussed herein, embodiments of the present invention embrace light therapy. In particular, embodiments of the present invention relate to systems and methods for dynamically distributing power of a light beam for use in administering light therapy. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A method for administering laser light therapy, the method comprising:
   providing a beam of a laser light source, wherein the beam includes a maximum peak power; and
   distributing power across the beam for use in administering light therapy on a patient, wherein the step for distributing power across the beam comprises using a holographic diffuser and a compound counter sink diffraction component lens.

2. A method as recited in claim 1, wherein the step for distributing power across the beam comprises a step for diffusing the beam.

3. A method as recited in claim 1, wherein the laser light therapy is for pain management.

4. A method as recited in claim 1, wherein the laser light therapy is for wound healing.

5. A method as recited in claim 1, wherein the light therapy is for at least one of:
   (i) chronic pain;
   (ii) a tension headache;
   (iii) a migraine headache;
   (iv) atypical facial pain;
   (v) a TMJ disorder;
   (vi) fibromyalgia;
   (vii) osteoarthritis;
   (viii) rheumatoid arthritis;
   (ix) pain associated with arthritis;
   (x) stiffness associated with arthritis;
   (xi) increasing local blood circulation;
   (xii) muscle spasm;
   (xiii) joint pain;
   (xiv) inflammation;
   (xv) Raynaud's Syndrome;
   (xvi) reflex sympathetic dystrophy;
   (xvii) a bum;
   (xviii) occipital neuralgia;
   (xix) neck-shoulder pain;
   (xx) frozen shoulder;
   (xxi) medial epicondylitis;
   (xxii) lateral epicondylitis;
   (xxiii) carpal tunnel syndrome;
   (xxiv) costochondritis;
   (xxv) spondylitis;
   (xxvi) low back strain;
   (xxvii) sciatica;
   (xxviii) hip arthritis;
   (xxix) knee arthritis;
   (xxx) an injury;
   (xxxi) a post surgical procedure;
   (xxxii) a post traumatic procedure;
   (xxxiii) achilles tendonitis;
   (xxxiv) an ankle sprain;
   (xxxv) plantar fasciitis;

(xxxvi) shingles; and
(xxxvii) postherpetic neuralgia.

6. A method for administering laser light therapy, the method comprising:
providing a beam of a laser light source, wherein the beam includes a maximum peak power; and
distributing power across the beam for use in administering light therapy on a patient, wherein the step for distributing power across the beam comprises a step for diffusing the beam, and wherein the step for diffusing comprises a step for using a holographic diffuser to diffuse the beam; and
attenuating the beam to reduce the maximum peak power, wherein the step for attenuating is performed by using a disk attenuator, and wherein at least a portion of the beam is diffused prior to being attenuated.

7. A method as recited in claim 6, wherein the light therapy is for pain management.

8. A method as recited in claim 6, wherein the light therapy is for wound healing.

9. A method as recited in claim 6, wherein the light therapy is for at least one of:
(i) chronic pain;
(ii) a tension headache;
(iii) a migraine headache;
(iv) atypical facial pain;
(v) a TMJ disorder;
(vi) fibromyalgia;
(vii) osteoarthritis;
(viii) rheumatoid arthritis;
(ix) pain associated with arthritis;
(x) stiffness associated with arthritis;
(xi) increasing local blood circulation;
(xii) muscle spasm;
(xiii) joint pain;
(xiv) inflammation;
(xv) Raynaud's Syndrome;
(xvi) reflex sympathetic dystrophy;
(xvii) a burn;
(xviii) occipital neuralgia;
(xix) neck-shoulder pain;
(xx) frozen shoulder;
(xxi) medial epicondylitis;
(xxii) lateral epicondylitis;
(xxiii) carpal tunnel syndrome;
(xxiv) costochondritis;
(xxv) spondylitis;
(xxvi) low back strain;
(xxvii) sciatica;
(xxviii) hip arthritis;
(xxix) knee arthritis;
(xxx) an injury;
(xxxi) a post surgical procedure;
(xxxii) a post traumatic procedure;
(xxxiii) achilles tendonitis;
(xxxiv) an ankle sprain;
(xxxv) plantar fasciitis;
(xxxvi) shingles; and
(xxxvii) postherpetic neuralgia.

10. A method for administering laser light therapy, the method comprising:
providing a beam of a laser light source, wherein the beam includes a maximum peak power; and
distributing power across the beam for use in administering light therapy on a patient, wherein the step for distributing power across the beam comprises a step for diffusing the beam, and wherein the step for diffusing comprises a step for using a compound counter sink diffraction component lens to diffuse the beam, wherein the lens provides a defocused diffusion of the beam.

11. A method as recited in claim 10, wherein the lens performs at least one of:
spreading out power of the beam by using a curve in the lens; and
reducing power loss of the beam.

12. A method as recited in claim 10, wherein the light therapy is for pain management.

13. A method as recited in claim 10, wherein the light therapy is for wound healing.

14. A method as recited in claim 10, wherein the light therapy is for at least one of:
(i) chronic pain;
(ii) a tension headache;
(iii) a migraine headache;
(iv) atypical facial pain;
(v) a TMJ disorder;
(vi) fibromyalgia;
(vii) osteoarthritis;
(viii) rheumatoid arthritis;
(ix) pain associated with arthritis;
(x) stiffness associated with arthritis;
(xi) increasing local blood circulation;
(xii) muscle spasm;
(xiii) joint pain;
(xiv) inflammation;
(xv) Raynaud's Syndrome;
(xvi) reflex sympathetic dystrophy;
(xvii) a burn;
(xviii) occipital neuralgia;
(xix) neck-shoulder pain;
(xx) frozen shoulder;
(xxi) medial epicondylitis;
(xxii) lateral epicondylitis;
(xxiii) carpal tunnel syndrome;
(xxiv) costochondritis;
(xxv) spondylitis;
(xxvi) low back strain;
(xxvii) sciatica;
(xxviii) hip arthritis;
(xxix) knee arthritis;
(xxx) an injury;
(xxxi) a post surgical procedure;
(xxxii) a post traumatic procedure;
(xxxiii) achilles tendonitis;
(xxxiv) an ankle sprain;
(xxxv) plantar fasciitis;
(xxxvi) shingles; and
(xxxvii) postherpetic neuralgia.

15. A method for dynamically distributing power of a light beam for use in administering light therapy, the method comprising:
providing a beam from a light source having a maximum peak power; and
modifying the beam for use in administering light therapy by diffusing the beam to allocate power across the beam, wherein the step for modifying the beam further includes attenuating the beam, and wherein at least a portion of the beam is first diffused and then attenuated.

16. A method as recited in claim 15, wherein the light source is a laser light source, and wherein the step for modifying comprises selectively diffusing the beam.

17. A method as recited in claim 15, wherein the step for diffusing comprises a step for using a holographic diffuser to diffuse the beam.

18. A method as recited in claim 15, wherein the light therapy is for pain management.

19. A method as recited in claim 15, wherein the light therapy is for wound healing.

20. A method as recited in claim 15, wherein the light therapy is for at least one of:
(i) chronic pain;
(ii) a tension headache;
(iii) a migraine headache;
(iv) atypical facial pain;
(v) a TMJ disorder;
(vi) fibromyalgia;
(vii) osteoarthritis;
(viii) rheumatoid arthritis;
(ix) pain associated with arthritis;
(x) stiffness associated with arthritis;
(xi) increasing local blood circulation;
(xii) muscle spasm;
(xiii) joint pain;
(xiv) inflammation;
(xv) Raynaud's Syndrome;
(xvi) reflex sympathetic dystrophy;
(xvii) a burn;
(xviii) occipital neuralgia;
(xix) neck-shoulder pain;
(xx) frozen shoulder;
(xxi) medial epicondylitis;
(xxii) lateral epicondylitis;
(xxiii) carpal tunnel syndrome;
(xxiv) costochondritis;
(xxv) spondylitis;
(xxvi) low back strain;
(xxvii) sciatica;
(xxviii) hip arthritis;
(xxix) knee arthritis;
(xxx) an injury;
(xxxi) a post surgical procedure;
(xxxii) a post traumatic procedure;
(xxxiii) achilles tendonitis;
(xxxiv) an ankle sprain;
(xxxv) plantar fasciitis;
(xxxvi) shingles; and
(xxxvii) postherpetic neuralgia.

21. A laser light probe comprising:
a laser light source configured to selectively emit a laser beam when actuated, the laser beam having a maximum peak power;
a power source coupled to the laser light source to power the laser light source and cause the laser beam to be emitted therefrom; and
a beam adapter aligned with the laser light source to cause the laser beam to extend through the beam adapter for dynamic distribution of the laser beam, the beam adapter comprising a diffusing component configured to distribute power across the laser beam, wherein the diffusing component comprises a holographic diffuser, and wherein the beam adapter further comprises at least one of:
(i) an attenuator aligned with the holographic diffuser;
(ii) a counter sink diffraction component aligned with the holographic diffuser; and
(iii) a compound counter sink diffraction component lens aligned with a counter sink diffraction component and the holographic diffuser.

22. A laser light probe as recited in claim 21, wherein the beam adapter further comprises an attenuating component configured to attenuate the maximum peak power.

23. A laser light probe as recited in claim 21, wherein the beam adapter further comprises a lens that is configured to distribute power.

24. A laser light probe as recited in claim 21, further comprising an actuator coupled to the power source to selectively actuate the laser light source.

25. A laser light probe as recited in claim 24, wherein the actuator comprises a proximity detector.

26. A laser light probe as recited in claim 24, further comprising an indicator coupled to the power source to communicate whether the laser light source is currently actuated.

* * * * *